United States Patent
Wehrli

(10) Patent No.: US 8,420,835 B2
(45) Date of Patent: Apr. 16, 2013

(54) PROCESS FOR PRODUCING CARNOSOL FROM CARNOSIC ACID

(75) Inventor: Christof Wehrli, Witterswil (CH)

(73) Assignee: DSM IP Assets B.V., Heerlen (NL)

( * ) Notice: Subject to any disclaimer, the term of this patent is extended or adjusted under 35 U.S.C. 154(b) by 263 days.

(21) Appl. No.: 12/738,923

(22) PCT Filed: Sep. 30, 2008

(86) PCT No.: PCT/EP2008/008289
§ 371 (c)(1),
(2), (4) Date: Apr. 20, 2010

(87) PCT Pub. No.: WO2009/052924
PCT Pub. Date: Apr. 30, 2009

(65) Prior Publication Data
US 2010/0217036 A1    Aug. 26, 2010

(30) Foreign Application Priority Data

Oct. 22, 2007  (EP) .................................... 07020610
Nov. 21, 2007  (EP) .................................... 07022529
Apr. 15, 2008  (EP) .................................... 08007339

(51) Int. Cl.
*C07D 493/08*   (2006.01)
*A61K 31/352*   (2006.01)

(52) U.S. Cl.
USPC ............................. 549/281; 514/453; 514/454

(58) Field of Classification Search ........................ None
See application file for complete search history.

(56) References Cited

U.S. PATENT DOCUMENTS 6,638,523 B1    10/2003   Miyazaki et al.

FOREIGN PATENT DOCUMENTS

FR    2 899 768       10/2007
JP    2003-261454      9/2003

OTHER PUBLICATIONS

International Search Report for PCT/EP2008/008289, mailed Jan. 13, 2009.
Written Opinion of the International Searching Authority for PCT/EP2008/008289, mailed Jan. 13, 2009.
Masuda, T. et al., "Recover Mechanism of the Antioxidant Activity from Carnosic Acid Quinone, an Oxidized Sage and Rosemary Antioxidant", J. Agric. Food Chem., vol. 50, No. 21, (2002), pp. 5863-5869.
Masuda, T. et al., "Antioxidant Mechanism of Carnosic Acid: Structural Identification of Two Oxidation Products", Agric. Food Chem., vol. 49, No. 11, (2001), pp. 5560-5565.
Marrero, J.G. et al., "Semisynthesis of Rosmanol and its Derivatives, Easy Access to Abietatriene Diterpenes Isolated from the Genus *Salvia* with Biological Activities", J. Nat. Prod., vol. 65, No. 7, (2002), pp. 986-989.
Wenkert, E. et al., "Chemical Artifacts from the Family *Labiatae*", J. Org. Chem., vol. 30, (1965), pp. 2931-2934.
Database WPI, Derwent Publications Ltd., Accession No. 2003-884059 & JP 2003-261454, (Sep. 16, 2003).

*Primary Examiner* — Brian J Davis
(74) *Attorney, Agent, or Firm* — Nixon & Vanderhye P.C.

(57) ABSTRACT

Novel catalytic processes for the production of carnosol from carnosic acid are presented. The carnosic acid may be in pure form, in an impure form, part of a plant extract, or may be present in rosemary needles. The catalyst may be iron, iron salts, a minor amount of water, rosemary needles, or a mixture thereof.

26 Claims, No Drawings

PROCESS FOR PRODUCING CARNOSOL FROM CARNOSIC ACID

This application is the U.S. national phase of International Application No. PCT/EP2008/008289 filed 30 Sep. 2008, which designated the U.S. and claims priority to EP Application No. 07020610.7 filed 22 Oct. 2007; EP Application No. 07022529.7 filed 21 Nov. 2007; and EP Application No. 08007339.8 filed 15 Apr. 2008, the entire contents of each of which are hereby incorporated by reference.

BRIEF DESCRIPTION OF THE INVENTION

This invention relates to new processes for the production of carnosol from carnosic acid, which may be present in rosemary extract, rosemary needles, or in sage extracts using a catalyst.

BACKGROUND

Rosemary (*Rosmarinus officialis*) is a woody perennial herb with fragrant evergreen needle-like leaves native to the Mediterranean region. It is known as an herb commonly used in Mediterranean cuisine. Its dried form is high in iron, calcium and Vitamin B6. It also contains a carnosol, a polyphenol, which is an antioxidant and has recently been described as an anti-carcinogen (Lo et al 2002 *Carcinogenesis* 23(6): 983-991), working by suppressing the NF-κB pathway.

Lipophilic rosemary or sage extracts contain approximately 10-30% carnosic acid.

A process for synthesizing carnosol from carnosic acid was published by Marrero et al 2002 *J. Natural Products* 65:986-989. A "quantitative conversion" to carnosol is described whereby carnosic acid is dissolved in acetone and molecular oxygen was bubbled through the solution. However, despite numerous repetitions of this scheme, it was not repeatable, and virtually no carnosol was formed.

It would be desirable to have an easy, efficient process for transforming the carnosic acid into the biologically active form carnosol, especially if the extraction and transformation were essentially the same step.

DETAILED DESCRIPTION OF THE INVENTION

It has been found, in accordance with this invention, that carnosic acid can be converted into carnosol by an oxidation process, provided that there is a catalyst present. The catalyst can either be: a catalytic amount of iron or iron salts, a minor amount of water, rosemary needles, or mixtures thereof. Choice of the catalyst will depend on other parameters of the reaction, which are presented in more detail below. Thus, one process of the invention comprises:

a) exposing carnosic acid to a solvent comprising a catalyst selected from the group consisting of minor amounts of water, iron, an iron salt, rosemary needles and mixtures thereof, and b) introducing oxygen to produce carnosol.

While not wishing to be bound by theory, the conversion of carnosic acid is thought to occur in two stages. The first step is considered to be the oxidation to the quinone (although this has not yet been demonstrated by spectroscopy), followed by rearrangement to carnosol. The two stages may occur at same time or as discrete steps in a one-pot procedure, or may take place in separate reactions.

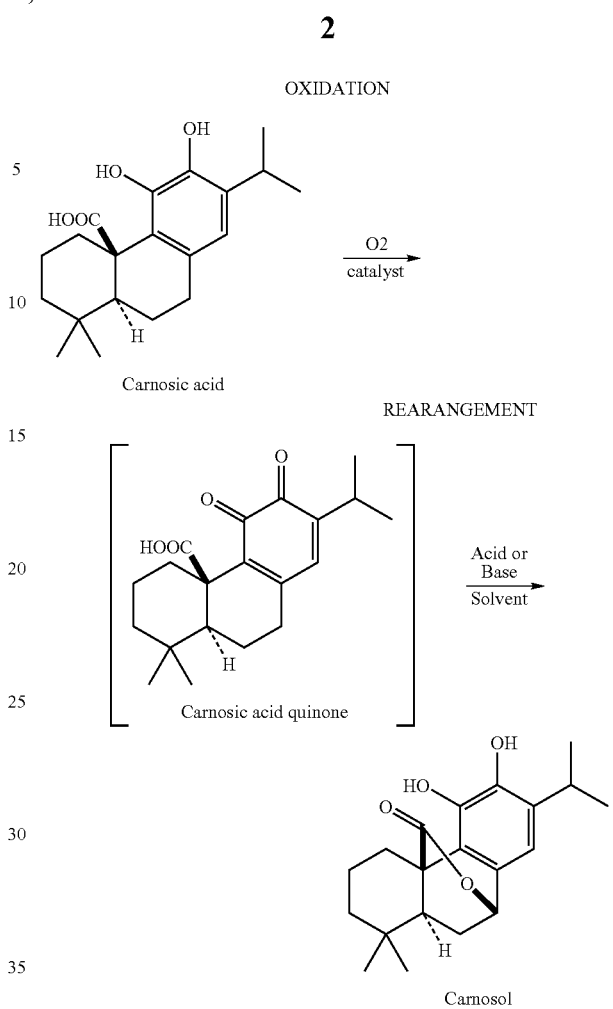

Also, in accordance with this invention, it has been found that the intermediate carnosic acid quinone can undergo rearrangement to produce carnosol in the presence of an acid or a weak base. Thus, this invention also comprises a process of producing carnosol from a carnosic acid quinone comprising exposing carnosic acid quinone to an acid or a weak base.

The carnosol-containing compositions produced by the reactions also form an embodiment of this invention. Thus this invention also comprises carnosol compositions made by any of the processes described herein, as well as to end products, such as nutraceuticals and pharmaceutical products which contain these carnosol-containing compositions.

The starting material for this reaction may be any source of carnosic acid. It may be purified carnosic acid itself, or carnosic acid which is not in a purified form, such as a rosemary extract or other plant extract which contains carnosic acid (such as sage, *Salvia* spp.). In another embodiment of the invention it may be rosemary leaves (needles).

Catalysts

A. Oxidation Catalyst is Iron:

It has been found, in accordance with this invention, that an iron catalyst, selected from the group consisting of iron, iron salts and mixtures thereof, acts as an oxidation catalyst, converting the carnosic acid to the intermediate quinone. Without the iron or iron salts, the oxidation of carnosic acid to the intermediate quinone is quite slow, and in dry solvents is not readily measurable.

The iron salt may be any commonly used form of iron salts, (such as iron chloride, iron bromide, iron sulfate, iron acetate, iron citrate, iron gluconate, iron lactate, iron nitrates, iron hydroxides, and iron oxides, etc.). As used throughout the specification and claims, the term "iron salts" is intended to include both ferric salts and ferrous salts as well as the hydrates thereof.

If the solvent is acidic and stored in an iron container, the solvent will take up iron, and this amount is usually sufficient for purposes of this invention. The amounts of iron/iron salt needed are quite low: at least about 0.0001-20 mole % (based on carnosic acid), with a preferred amount of from at least about 0.01 to 10 mole %, and more preferred from at least about 0.1 to 5 mole %. Higher amounts of iron may be present, of course; however in high amounts no particular advantage is seen.

B. Oxidation Catalyst is Water

In processes where an iron catalyst is not used, water can be used a catalyst and added to the solvent to increase the speed of the reaction. Water, in the absence of iron or iron salts, increases the reaction rate in non-protic solvents. In nonpolar and medium polar solvents (such as dichloromethane, ethylacetate, butylacetate, acetone and SF-CO2), the reaction rate is more or less absent in water-free solvents. The amount of water should be between about 0.1-60%, preferably about 2-40%, and more preferably about 3-30%, based on the amount of solvent used. The water can either be added to the reaction mixture, or wet solvents can be used.

C. Oxidation Catalyst is Rosemary Needles (Leaves)

In another embodiment of the invention, the rosemary needles themselves act as a catalyst during this extraction/conversion process. For economic reasons, rosemary needles are often preferred. If they are used fresh, no additional processing need be done prior to the reaction. The natural water present (about 75%) in the needles will be sufficient to catalyze the reaction, so no additional water need be added to the solvent, (of course, additional water may be added if desired). However, if dried rosemary leaves are used, then some water should be added to the solvent.

With rosemary needles, the reaction rate was found to increase when a nonpolar to medium polar solvent was used (such as dichloromethane, ethylacetate, butylacetate and acetone) or in SF CO2. While the addition of a base is optional, use of a weak base helps to increase the rate of the quinone to carnosol step. Preferred weak bases are Na- or K-hydrogen carbonate or acetate.

Solvents

Solvents for Use with Iron Catalysts

The solvents which can be used in the presence of an iron catalyst are virtually any solvent in which carnosic acid can be dissolved or is at least partially soluble. The solvent may be:

a neutral solvent, such as an ether (R2OR2 where R2, which may be the same or different, is C1 to C4), or an ester R1-COOR2 where R1 is H, or C1 to C3; and R2 is C1 to C4 (such as ethylacetate, butylacetate), or a ketone (such as acetone, methylethylketone or diethylketone) or dichloromethane, or an alcohol R1 OH (such as ethanol, or isopropanol) where R1 is C1 to C4, or sub- or supercritical carbon dioxide "SF-CO2"; or an acidic solvent having from 2 to 4 carbon atoms (such as acetic acid, propionic acid or isobutyric acid); or any mixture of the above solvents.

The preferred solvents are: dichloromethane, SF-CO2, acetone, ethylacetate and acetic acid, propionic and isobutyric acid. Neutral solvents are less preferred, as there was non-selective oxidation, with the exception of chlorinated solvents. The most preferred solvent is acetic acid, especially if the intended use of the carnosol is a food or pharmaceutical product.

Solvents for Use Without Iron Catalysts

The solvents which can be used in the absence of an iron catalyst are virtually any solvent in which carnosic acid can be dissolved or is at least partially soluble. The solvent may be an:

acidic solvent having from 2 to 4 carbon atoms (such as acetic acid, propionic acid or isobutyric acid);

a neutral solvent, such as an ether (R2OR2 where R2, which may be the same or different, is C1 to C4), or an ester R1-COOR2 where R1 is H, or C1 to C3; and R2 is C1 to C4 (such as ethylacetate, butylacetate), or a ketone (such as acetone, methylethylketone or diethylketone) or dichloromethane, or an alcohol R1 OH (such as ethanol, or isopropanol) where R1 is C1 to C4, or sub- or supercritical carbon dioxide "SF-CO2";

or any mixture of the above solvents.

In cases of neutral solvents some water should be present, otherwise the reaction is nearly absent.

The preferred solvents are: dichloromethane, SF-CO2, acetic acid, propionic and isobutyric acid, where a selective oxidation transforms carnosic acid into carnosol. The most preferred solvent is acetic acid, especially if the intended use of the carnosol is a food or pharmaceutical product.

Solvents for Use with Rosemary Needles (Leaves) as Catalysts (No Iron)

The solvents which can be used are virtually any solvent in which carnosic acid can be dissolved or is at least partially soluble. The solvent may be:

an neutral solvent, such as an ether R2OR2 where R2, which may be the same or different is C1 to C4, or an ester R1-COOR2 where R1 is H, or C1 to C3; and R2 is C1 to C4 (such as ethylacetate, butylacetate), or a ketone (such as acetone, methylethylketone or diethylketone) or dichloromethane, or an alcohol R1OH (such as ethanol, or isopropanol) where R1 is C1 to C4, or sub- or supercritical carbon dioxide "SF-CO2"; or an acidic solvent having from 2 to 4 carbon atoms (such as acetic acid, propionic acid or isobutyric acid).

The preferred solvents are ethylacetate, acetone, dichloromethane, and SF-CO2.

Catalyst for the Transformation of the Intermediate Quinone

The carnosic acid in a solvent and a catalyst, is then reacted with oxygen, In one embodiment, the oxidation reaction occurs either in the presence of a base or an acid. Alternatively, the base or the acid can also be added at a later stage of the oxidation, or after the formation of the intermediate quinone. In another alternative, the intermediate can be formed separately and then treated with an acid or base to form carnosol.

The base or the acid is believed to increase the rate of transformation of the intermediate, which is presumed to be a quinone.

For purposes of this reaction, the base can be present in any conveniently desired amount. If a base is chosen as a catalyst, then generally, the base will increase the reaction rate; i.e. the more base that is present, the faster the transformation will take place. Generally the base should be present in an amount of 0%-400 mole % based on the amount of carnosic acid. A preferred range is from about 10 to 300 mole %, and more preferably 80-200 mole %.

The choice of base will also be affected by the solvent chosen. In acidic solvent situations (i.e. SF-CO2, acetic acid, or other R—COOH), both strong and weak bases gave similar results. If an acidic solvent such as acetic acid is used, then in principle any base can be used, as all form the corresponding acetate. Thus, the base can be selected from the group consisting of; sodium- or potassium-(hydroxide, carbonate, hydrogen carbonate, acetate, propionate, phosphate); magnesium hydroxide, and mixtures thereof.

If the solvent used is a neutral one (such as dichloromethane, or ethylacetate) weak bases such as $NaHCO_3$, KOAc, $Na_2HPO_4$, and $Mg(OH)_2$ are preferred.

Preferred bases are generally Na- or K-hydrogen carbonate or acetate.

Alternatively, an acid can serve the same purpose as the base. If an acid is choosen as the catalyst, then virtually any strong acid can be used; mineral acids are preferred, such as: sulfuric acid, hydrochloric acid, hydrobromic acid, perchloric acid, nitric acid, or an sulfonic acid like p-toluenesulfonic acid. Generally the acid should be present in an amount of 0%-100 mole % based on the amount of carnosic acid. A preferred range is from about 1 to 40 mole %, and more preferably 2-20 mole % based on the amount of carnosic acid.

The use of acids as transformation catalysts is preferred in solvents with a low water content.

Oxidation Agent—Used Regardless of Catalyst

Oxygen (either as pure oxygen or air) may be used as the oxidation agent. Increasing the partial pressure of the oxygen increases the reaction rate. A partial pressure of oxygen of from about 0.1 to about 20 bar is preferred; a more preferred range is from about 0.2 to 10 bar; and an even more preferred range is from about 1-10 bar.

Temperature—Regardless of Catalyst

In general, a higher temperature will result in a faster reaction. However, the reaction becomes less selective at higher temperatures. A preferred temperature range is from about 0-100° C., a more preferred range is from about 10-80° C., and an even more preferred range is from about 20-60° C.

Optional Crystallization Step

Regardless of which or the above-described procedures are used, it is possible to increase the purity of the final carnosol obtained by subjecting the reaction product to a crystallization step. Crystallization may be accomplished using any conventional means; in most applications the preferred solvent is acetic acid. In some applications, crystals can be produced with a carnosol content exceeding 90%.

End Product Uses

The end product of these described reactions, while containing carnosol, also contain other reaction by-products. These compositions containing both carnosol and other reaction by-products hereinafter referred to as "carnosol process compositions", can be used directly without further purification or other processing in the use of foods and/or nutraceuticals for various uses.

The term "nutraceutical" as used herein denotes usefulness in both nutritional and pharmaceutical fields of application. Thus, novel nutraceutical compositions containing the carnosol process compositions can be used as supplements to food and beverages and as pharmaceutical formulations for enteral or parenteral application which may be solid formulations, such as capsules or tablets, or liquid formulations, such as solutions or suspensions.

The nutraceutical compositions according to the present invention may further contain protective hydrocolloids (such as gums, proteins, modified starches), binders, film-forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste-masking agents, weighting agents, jellyfying agents, gel-forming agents, antioxidants and antimicrobials.

Moreover, a multi-vitamin and mineral supplement may be added to nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The nutraceutical compositions according to the present invention may be in any galenic form that is suitable for administering to the body, especially in any form that is conventional for oral administration, e.g. in solid forms such as (additives/supplements for) food or feed, food or feed premix, fortified food or feed, tablets, pills, granules, dragées, capsules and effervescent formulations, such as powders and tablets, or in liquid forms, such as solutions, emulsions or suspensions as e.g. beverages, pastes and oily suspensions. The pastes may be incorporated in hard or soft shell capsules, whereby the capsules feature e.g. a matrix of (fish, swine, poultry, cow) gelatine, plant proteins or lignin sulfonate. Examples for other application forms are those for transdermal, parenteral or injectable administration. The dietary and pharmaceutical compositions may be in the form of controlled (delayed) release formulations.

Feed encompasses any feed given to pet animals, farm animals, animals used for the fur industry and aquaculture animals. It also encompasses treats given to pet animals (e.g. dogs and cats).

Examples of food are dairy products including, for example, margarines, spreads, butter, cheese, yoghurts or milk-drinks. Examples of fortified food are cereal bars, bakery items, such as cakes and cookies. Beverages encompass non-alcoholic and alcoholic drinks as well as liquid preparations to be added to drinking water and liquid food. Non-alcoholic drinks are e.g. soft drinks, sports drinks, fruit juices, lemonades, teas and milk-based drinks. Liquid foods are e.g. soups and dairy products. The nutraceutical composition containing carnosol process compositions may be added to a soft drink, an energy bar, or a candy, such that an adult consumes from about 10 to 1000 mg carnosol per daily serving, preferably from about 50 to 750 mg per daily serving, or more preferably from about 100 to 500 mg per daily serving.

If the nutraceutical composition is a pharmaceutical formulation the composition further contains pharmaceutically acceptable excipients, diluents or adjuvants. Standard techniques may be used for their formulation, as e.g. disclosed in *Remington's Pharmaceutical Sciences, 20th edition* Williams & Wilkins, PA, USA. For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

The nutraceuticals can be used to maintain or improve various conditions, such as for its anti-inflammation properties, to maintain or improve mind or mood and for joint health.

The following non-limiting Examples are presented to better illustrate the invention.

Example 1

Control Experiment

A solution of 0.132 g carnosic acid (content=90% carnosic acid, 2% carnosol) in 30 ml acetone was stirred in a 10 ml reaction vessel at ambient in an atmosphere of oxygen for 23 h. These are essentially the conditions described in J. G. Marrero, L. S. Andres, J. G. Luis; J. *Nat. Prod.* (2002), 65, 986-989. The solution contained: 88% carnosic acid, and only 3% carnosol

Example 2

Iron as Catalyst with Rosemary Extract

Preparation of solid free rosemary extract:

102 g rosemary extract "Naturex CS" was stirred in 320 ml ethylacetate and filtered to remove the insolubles. The filtrate was evaporated to dryness. The residue (34.3 g) contained 47% carnosic acid, 7.5% carnosol [w %].

To 34 g of the above solid free rosemary extract (56 mmole) was added 280 ml acetic acid and 5.7 g sodium hydrogen carbonate, and 15 mg iron chloride hexahydrate in 50 ml of water. This was added to a 500 ml reaction vessel. The mixture was stirred at ambient in an atmosphere of oxygen for 4d. The slurry of carnosol was filtrated and dried in the vacuum. 12.5 g carnosol of purity=92%. Yield=63% [mol %]

Example 3

Iron as Catalyst with Carnosic Acid

In a 10 ml reaction vessel in an atmosphere of oxygen, a solution of 0.10 g carnosic acid (content=90% carnosic acid, 2% carnosol) in 2.5 ml acetic acid, 0.5 ml water and 34 mg sodium hydrogen carbonate was added a solution of 0.01 mol/l iron trichloride in acetic acid (as shown in Table 1, below). The mixture in the vessel was stirred at ambient in an atmosphere of oxygen for 1 h. The solution was analyzed for turnover.

TABLE 1

| Metal [mol %] | Carnosic acid [%] | Carnosol + carnosic acid quinone [%] |
|---|---|---|
| 1 mol % $FeCl_3 \cdot nH_2O$ | 4 | 66 |
| 0.1 mol % $FeCl_3 \cdot nH_2O$ | 26 | 57 |
| 0.01 mol % $FeCl_3 \cdot nH_2O$ | 54 | 38 |
| no catalyst | 89 | 9 |
| 0.1 mol % $CuCl_2$ | 92 | 4 |
| 0.1 mol % $CrCl_3$ | 94 | 4 |
| 0.1 mol % $KMnO_4$ | 93 | 5 |

Example 4

Water as Catalyst with Rosemary Extract (SF-CO2)

Preparation of Solid Free Rosemary Extract 9.6 g rosemary extract "Naturex CS" commercially available from Naturex; (d'Agroparc-BP 1218-84911 Avignon cedex 9) was stirred in 30 ml ethylacetate and filtered to remove the insolubles. The filtrate was evaporated to dryness. The residue (3.2 g) contained 47% carnosic acid, 7.5% carnosol [w %]

In a 25 ml stainless steel autoclave was mixed: 3.2 g of the solids-free rosemary extract (above) and a solution of 57 mg sodium hydrogen carbonate in 1 ml water. The tightly closed autoclave was pressurized to 10 bar with oxygen, followed by filling it with carbon dioxide to 95 bar at ambient. The mixture in the autoclave was heated to 60° C. (pressure rose to 160 bar) and was shaken with a frequency of 240 on a shaker (Lab Shaker; LSR/L-V; Adolf Kuehner AG) for 48 hours. The mixture was cooled to 20° C. and the pressure was relieved. The solid residue was crystallized from acetic acid to yield 1.23 g crystals of carnosol with a content of 93%. Yield of isolated carnosol=65% [mol %].

Example 5

Water as Catalyst with Carnosic Acid

In a 10 ml reaction vessel in an atmosphere of oxygen was added to 0.10 g carnosic acid (content=90%) 2.5 ml acetic acid and a solution of 17 mg sodium acetate in 0.5 ml of water. The mixture in the vessel was stirred at ambient in an atmosphere of oxygen for 6d until most of the carnosic acid was converted to carnosol. The solution was analyzed for the content of carnosol. It was obtained yield=68% [mol %].

Example 6

Solvents with Water

Various solvents were evaluate in the reaction of carnosic acid to carnosol with water. 0.30 g of rosemary extract (obtained in accordance with previous examples), 8.8 ml of a solvent, 1.8 ml of water and 30 mg sodium hydrogen carbonate were reacted under ambient temperatures of days in 1 bar air (partial pressure of oxygen was 0.2 bar) [a %] is area percent determined from HPLC.

Results are presented in the table below:

| SOLVENT | Time [d] | Carnosic acid [a %] | Carnosol + Carnosic acid quinone [a %] | Comment |
|---|---|---|---|---|
| Starting Extract: | 0 | 63 | 11 | Initial value |
| Dichloromethane | 2 | 4 | 42 | |
| Acetic acid | 7 | 24 | 41 | |
| Methyl tert butyl ether | 7 | 5 | 38 | overoxidation |
| Ethylacetate | 7 | 7 | 36 | overoxidation |
| Propionic acid | 7 | 36 | 32 | |
| Isobutyric acid | 7 | 35 | 30 | |
| Hexane | 7 | 15 | 27 | overoxidation |
| Water | 7 | 21 | 17 | overoxidation |
| Formic acid | 7 | 66 | 11 | no reaction |
| Acetone | 7 | <2 | <2 | overoxidation |
| Acetonitrile | 7 | <2 | <2 | overoxidation |
| Ethanol | 7 | <2 | <2 | overoxidation |

Example 7

Addition of a Base

The following were prepared in a manner similar to that described in Example 4.

| Base [mg] | Water [ml] | Carnosol Yield [mol %] |
|---|---|---|
| — | — | 19 |
| — | 0.5 ml | 35 |
| 17 mg NaOAc | — | 45 |
| 17 mg NaOAc | 0.5 ml | 68 |
| 34 mg NaHCO3 | 0.5 ml | 81 |

Example 8

Iron Salts and Strong Acids as Catalyst

In a 25 ml reaction vessel in an atmosphere of oxygen was added to 0.10 g carnosic acid (content=90%), 3 ml acetic acid, 27 µl of 0.001 molar FeCl3 solution in acetic acid and 81 µl of 0.033 molar p-toluenesulfonic acid solution in acetic acid. The mixture in the vessel was stirred at ambient in an atmosphere of oxygen for 30 h until most of the carnosic acid was converted to carnosol. The solution was analyzed for the content of carnosol. It was obtained yield=88% [mol %].

Example 9

Rosemary Needles/Extract

In a 25 ml stainless steel autoclave was filled:
100 mg rosemary extract (content=19% carnosic acid, 1.4% carnosol [w %]) and varying amounts of water (as shown in Table 2), varying amounts of fresh rosemary needles (content=10 mg carnosic acid, <1 mg carnosol) (as shown in Table 2).

The tightly closed autoclave was pressurized to 10 bar with oxygen, followed by filling it with carbon dioxide to 95 bar at ambient. The mixture in the autoclave was heated to 40° C. and shook for 15 h with a frequency of 240 on a shaker (Lab Shaker; LSR/L-V; Adolf Kuehner AG). The mixture was cooled to 20° C. and the pressure relieved. The residue was extracted with methanol, the solids filtered off and the filtrate was evaporated in the vacuum. This residue was analyzed for content of carnosic acid and carnosol [w %].

TABLE 2

|  | ml water | g Rosemary needles | carnosol [w %] | carnosic acid [w %] |
|---|---|---|---|---|
| 9a | 0 ml | 0 g | 2.1% | 17.4% |
| 9b | 0.75 ml | 0 g | 7.0% | 8.8% |
| 9c | 0 ml | 1.0 g | 20.5% | 4.0% |
| 9d | 0.75 ml | 1.0 g | 24.4% | 0.6% |

Example 10

Rosemary Needles

In a 10 ml reactor was mixed:
1 g of fresh rosemary needles (content=10 mg carnosic acid, <1 mg carnosol [w %]) and 2.5 ml ethylacetate and 0.3 ml saturated sodium hydrogen carbonate solution. The mixture in the reactor was stirred for 3 days at ambient in an air atmosphere. The solids were filtered off and washed with ethylacetate. The filtrate was evaporated in the vacuum to yield a residue of 71 mg with a content of 14.4% carnosol and <0.5% camosic acid [w %].

What it claimed is:

1. A process of producing carnosol from a carnosic acid quinone comprising exposing carnosic acid quinone to an acid or a base catalyst.

2. A process for converting carnosic acid to carnosol comprising the steps of:
   a) exposing carnosic acid to a solvent comprising a catalyst selected from the group consisting of minor amounts of water, iron, iron salts, rosemary needles and mixtures thereof, and
   b) introducing oxygen to produce carnosol.

3. A process according to claim 2 wherein the carnosic acid is present in a plant extract.

4. A process according to claim 2 wherein the oxygen is introduced in the presence of a base or an acid.

5. A process according to claim 2 wherein a base or an acid is added after the oxygen is introduced.

6. A process according to claim 2 wherein the oxygen is in air.

7. A process according to claim 2 wherein the catalyst is iron or iron salts.

8. A process according to claim 7 wherein the iron salts are selected from the group consisting of: ferric salts and ferrous salts of iron chloride, iron bromide, iron sulfate, iron nitrate, iron acetate, iron propionate, iron citrate, iron gluconate, iron lactates, iron oxides, iron hydroxides, hydrates thereof, and mixtures thereof.

9. A process according to claim 2 wherein the catalyst is a minor amount of water.

10. A process according to claim 2 wherein the carnosic acid is present in rosemary needles.

11. A process according to claim 2 wherein the catalyst is rosemary needles.

12. A process according to claim 2 wherein the solvent is selected from the group consisting of an acidic solvent having from 2 to 4 carbon atoms, an ether having a formula R2OR2 where R2, which may be the same or different, is C1 to C4, an ester having a formula R1-COOR2' where R1 is H, or C1 to C3, and R2' is C1 to C4, a ketone, dichloromethane, an alcohol having a formula R1'OH, where R1' is C1 to C4, sub- or supercritical carbon dioxide and mixtures thereof.

13. A process according to claim 2 wherein the solvent is selected from the group consisting of: an acidic solvent having from 2 to 4 carbon atoms or mixtures thereof.

14. A process according to claim 4 wherein the base is present in an amount of 0%-400 mole % based on the amount of carnosic acid.

15. A process according to claim 4 wherein the acid is present in an amount of 0%-100 mole % based on the amount of carnosic acid.

16. A process according to claim 15 wherein the acid is a strong mineral acid or a sulfonic acid.

17. A process according to claim 16 wherein the acid is selected from the group consisting of: sulfuric acid, hydrochloric acid, hydrobromic acid, perchloric acid, nitric acid and p-toluenesulfonic acid.

18. A process according to claim 15 wherein the acid is added after the oxygen is introduced.

19. A process according to claim 2 wherein the solvent is selected from the group consisting of acetic acid and SF-CO2.

20. A process according to claim 10 wherein the rosemary needles have natural water present therein.

21. A process according to claim 10 wherein the rosemary needles are dry and water is added to the solvent.

22. A process according to claim 2, further comprising a carnosol crystallization step.

23. A carnosol composition made by claim 2.

24. A carnosol composition according to claim 23 which is a food, feed, pharmaceutical composition or nutraceutical composition.

25. A nutraceutical comprising the carnosol composition according to claim 23, the nutraceutical being selected from the group consisting of food, food supplements, and beverages.

26. A medicament which comprises the carnosol composition according to claim 23.

* * * * *